United States Patent
Yamaguchi et al.

(10) Patent No.: US 12,124,112 B2
(45) Date of Patent: Oct. 22, 2024

(54) METHOD, MANUFACTURING METHOD, AND DESIGN SYSTEM FOR PROGRESSIVE POWER LENS

(71) Applicant: HOYA LENS THAILAND LTD., Pathumthani (TH)

(72) Inventors: Eiichiro Yamaguchi, Tokyo (JP); Toshiaki Sonehara, Tokyo (JP); Ayumu Ito, Tokyo (JP)

(73) Assignee: HOYA LENS THAILAND LTD., Pathumthani (TH)

( * ) Notice: Subject to any disclaimer, the term of this patent is extended or adjusted under 35 U.S.C. 154(b) by 486 days.

(21) Appl. No.: 17/491,129

(22) Filed: Sep. 30, 2021

(65) Prior Publication Data

US 2022/0100002 A1  Mar. 31, 2022

(30) Foreign Application Priority Data

Sep. 30, 2020  (JP) ................. 2020-164773

(51) Int. Cl.
*G02C 7/02* (2006.01)

(52) U.S. Cl.
CPC .................. *G02C 7/027* (2013.01)

(58) Field of Classification Search
CPC ........ G02C 7/027; G02C 7/025; G02C 7/061; G02C 7/088; G02C 7/086; G02C 7/081; G02C 7/08; G02C 7/06; G02C 7/065; G02C 7/63; G02C 7/066; G02C 7/024; G02C 7/028; G02C 13/005; G02C 2202/22; G02C 2202/04; A61B 3/113
USPC ............ 351/159.42, 159.43, 159.46, 159.73, 351/159.74, 159.76, 159.77
See application file for complete search history.

(56) References Cited

U.S. PATENT DOCUMENTS

| | | | |
|---|---|---|---|
| 2012/0092614 | A1 | 4/2012 | Drobe et al. |
| 2012/0113387 | A1 | 5/2012 | Mori et al. |
| 2017/0269377 | A1 | 9/2017 | Trumm et al. |

(Continued)

FOREIGN PATENT DOCUMENTS

| | | |
|---|---|---|
| EP | 3 686 656 A1 | 7/2020 |
| JP | 2014-195647 A | 10/2014 |
| JP | 2018-531706 A | 11/2018 |

OTHER PUBLICATIONS

Apr. 25, 2022 Extended Search Report issued in European Patent Application No. 21199334.0.

*Primary Examiner* — Travis S Fissel
(74) *Attorney, Agent, or Firm* — Oliff PLC

(57) ABSTRACT

Provided is technology that makes it possible to design a progressive power lens appropriate for visual behavior of a subject. A method for designing a progressive power lens includes: a step (a) of determining a relationship between a line-of-sight passage position on a surface of a progressive power lens through which a line of sight of a subject wearing the progressive power lens passes and a reactive accommodation amount that the subject exhibits when the line of sight passes through the line-of-sight passage position, based on visual behavior of the subject; a step (b) of judging whether or not the reactive accommodation amount is within an appropriate range; a step (c) of determining a correction method for correcting the progressive power lens based on a result of judgement made in the step (b); and a step (d) of correcting a design of the progressive power lens based on the correction method determined in the step (c).

7 Claims, 5 Drawing Sheets

(56) References Cited

U.S. PATENT DOCUMENTS

2018/0299696 A1  10/2018  Heslouis et al.
2018/0303336 A1  10/2018  Escalier et al.

S103 Head rotation amount ascertainment step
S104 Eyeball rotation amount ascertainment step
S110 Line-of-sight passage position and reactive accommodation amount ascertainment step
S120 Reactive accommodation amount judgement step
S130 Correction method determination step 101 Line-of-sight passage position and reactive accommodation amount ascertainment unit S201 Image capturing device arrangement step
S202 Pupil position imaging step
S110 Line-of-sight passage position and reactive accommodation amount ascertainment step
S120 Reactive accommodation amount judgement step
S130 Correction method determination step

METHOD, MANUFACTURING METHOD, AND DESIGN SYSTEM FOR PROGRESSIVE POWER LENS

BACKGROUND OF THE INVENTION

1. Field of the Invention

The present invention relates to a design method, a manufacturing method, and a design system for a progressive power lens.

2. Description of Related Art

It has been proposed that an eyeglass lens be designed considering visual behavior of a wearer. For example, JP 2014-195647A discloses a line-of-sight detection device with which it is possible to precisely measure a line of sight in a wide field of view by not only performing calibration based on a measurement result of eyeball movement when visual targets are gazed at in order by only moving eyeballs without moving the head, but also performing calibration based on a measurement result of eyeball movement when a line-of-sight direction is changed by moving the head while gazing at a predetermined visual target, and discloses designing an eyeglass lens based on an analysis result of gaze points and transmission points obtained using the line-of-sight detection device in which the calibration method is used.

Also, JP 2018-531706A discloses a method and a test device with which it is possible to measure a parameter of natural visual behavior of an individual easily and accurately, with consideration given to a posture assumed by the individual while reading, and focusing on near vision, which is important particularly in optical design of a progressive power eyeglass lens.

JP 2014-195647A and JP 2018-531706A are examples of related art.

SUMMARY OF THE INVENTION

According to JP 2014-195647A, a subject is required to wear a head band to which at least a forward visual field camera, an eyeball camera, an infrared LED, and a dichroic mirror are attached, and, in order to carry out the described calibration, the subject is required to move his head such that the line-of-sight direction is distributed over an angular range as wide as possible in the up-down direction and the left-right direction so as to encompass viewing angles to be measured, and such that a line of sight of the visual target does not go out of an eyeglass lens or is not interrupted by the frame of the eyeglass, the nose of the subject, or the like. That is, a state of exhibiting the accommodation ability in daily visual behavior of the wearer is not reproduced in the measurement, and accordingly, there is a possibility that unnecessary rotation of eyeballs and unnecessary rotation of the head are induced in the wearer.

According to JP 2018-531706A, a measurement result is processed using an appropriate coordinate system as a result of an image capturing device capturing an image of the head of a subject who is gazing in a direction in which an observation target position is observed, and therefore the subject need not wear any device. On the other hand, JP 2018-531706A merely discloses technology regarding a test.

An embodiment of the present invention has an object of providing technology with which it is possible to design a progressive power lens that is appropriate for visual behavior of a subject.

A first aspect of the present invention is a method for designing a progressive power lens, including:
a step (a) of determining a relationship between a line-of-sight passage position on a surface of a progressive power lens through which a line of sight of a subject wearing the progressive power lens passes and a reactive accommodation amount that the subject exhibits when the line of sight passes through the line-of-sight passage position, based on visual behavior of the subject;
a step (b) of judging whether or not the reactive accommodation amount is within an appropriate range;
a step (c) of determining a correction method for correcting the progressive power lens based on a result of judgement made in the step (b); and
a step (d) of correcting a design of the progressive power lens based on the correction method determined in the step (c).

A second aspect of the present invention is the method for designing a progressive power lens according to the first aspect,
wherein the visual behavior includes visual behavior with respect to objects that are at different distances in a forward depth direction in a sagittal plane of the subject.

A third aspect of the present invention is the method for designing a progressive power lens according to the first or the second aspect,
wherein the visual behavior includes a head rotation amount and an eyeball rotation amount that are generated by the subject.

A fourth aspect of the present invention is the method for designing a progressive power lens according to any one of the first to third aspects,
wherein, in the step (b), it is judged whether or not at least one of a ratio of the reactive accommodation amount to the maximum amplitude of accommodation of the subject and a ratio of the reactive accommodation amount to a refractive power at the line-of-sight passage position of the progressive power lens is within an appropriate range.

A fifth aspect of the present invention is the method for designing a progressive power lens according to any one of the first to fourth aspects,
wherein the correction method includes correction of an additional power of the progressive power lens.

A sixth aspect of the present invention is the method for designing a progressive power lens according to any one of the first to fifth aspects,
wherein the correction method includes correction of at least one of a progressive change start point and a progressive change end point of the progressive power lens.

A seventh aspect of the present invention is a method for judging a progressive power lens, including:
a step (a) of determining a relationship between a line-of-sight passage position on a surface of a progressive power lens through which a line of sight of a subject wearing the progressive power lens passes and a reactive accommodation amount that the subject exhibits when the line of sight passes through the line-of-sight passage position, based on visual behavior of the subject; and
a step (b) of judging whether or not the reactive accommodation amount is within an appropriate range.

An eighth aspect of the present invention is a method for manufacturing a progressive power lens, including:
a step (a) of determining a relationship between a line-of-sight passage position on a surface of a progressive power lens through which a line of sight of a subject wearing the progressive power lens passes and a reactive accommodation amount that the subject exhibits when the line of sight passes through the line-of-sight passage position, based on visual behavior of the subject;

a step (b) of judging whether or not the reactive accommodation amount is within an appropriate range;

a step (c) of determining a correction method for correcting the progressive power lens based on a result of judgement made in the step (b);

a step (d) of correcting a design of the progressive power lens based on the correction method determined in the step (c); and a step (e) of processing the progressive power lens based on the design corrected in the step (d).

A ninth aspect of the present invention is a system for designing a progressive power lens, including:

a judgement unit configured to judge whether or not a reactive accommodation amount is within an appropriate range, based on a relationship between a line-of-sight passage position on a surface of a progressive power lens through which a line of sight of a subject wearing the progressive power lens passes and the reactive accommodation amount that the subject exhibits when the line of sight passes through the line-of-sight passage position, the relationship being determined based on visual behavior of the subject; and a correction unit configured to correct a design of the progressive power lens based on a result of judgement made by the judgement unit.

A tenth aspect of the present invention is a system for designing a progressive power lens, including:

a line-of-sight passage position and reactive accommodation amount ascertainment unit configured to ascertain a line-of-sight passage position on a surface of a progressive power lens through which a line of sight of a subject wearing the progressive power lens passes and a reactive accommodation amount that the subject exhibits when the line of sight passes through the line-of-sight passage position, based on visual behavior of the subject;

a judgement unit configured to judge whether or not the reactive accommodation amount is within an appropriate range; and a correction unit configured to correct a design of the progressive power lens based on a result of judgement made by the judgement unit.

According to an embodiment of the present invention, it is possible to design a progressive power lens that is appropriate for visual behavior of a subject.

DETAILED DESCRIPTION OF THE INVENTION

The following describes embodiments of the present invention with reference to the drawings. The present invention is not limited to these examples, but is defined by the claims, and is intended to encompass all modifications within the meanings and scope that are equivalent to the claims.

First Embodiment of the Present Invention (1) Method for Designing Progressive Power Lens First, a design method, a judgement method, and a manufacturing method for a progressive power lens according to the present embodiment will be described.

Figure 1:
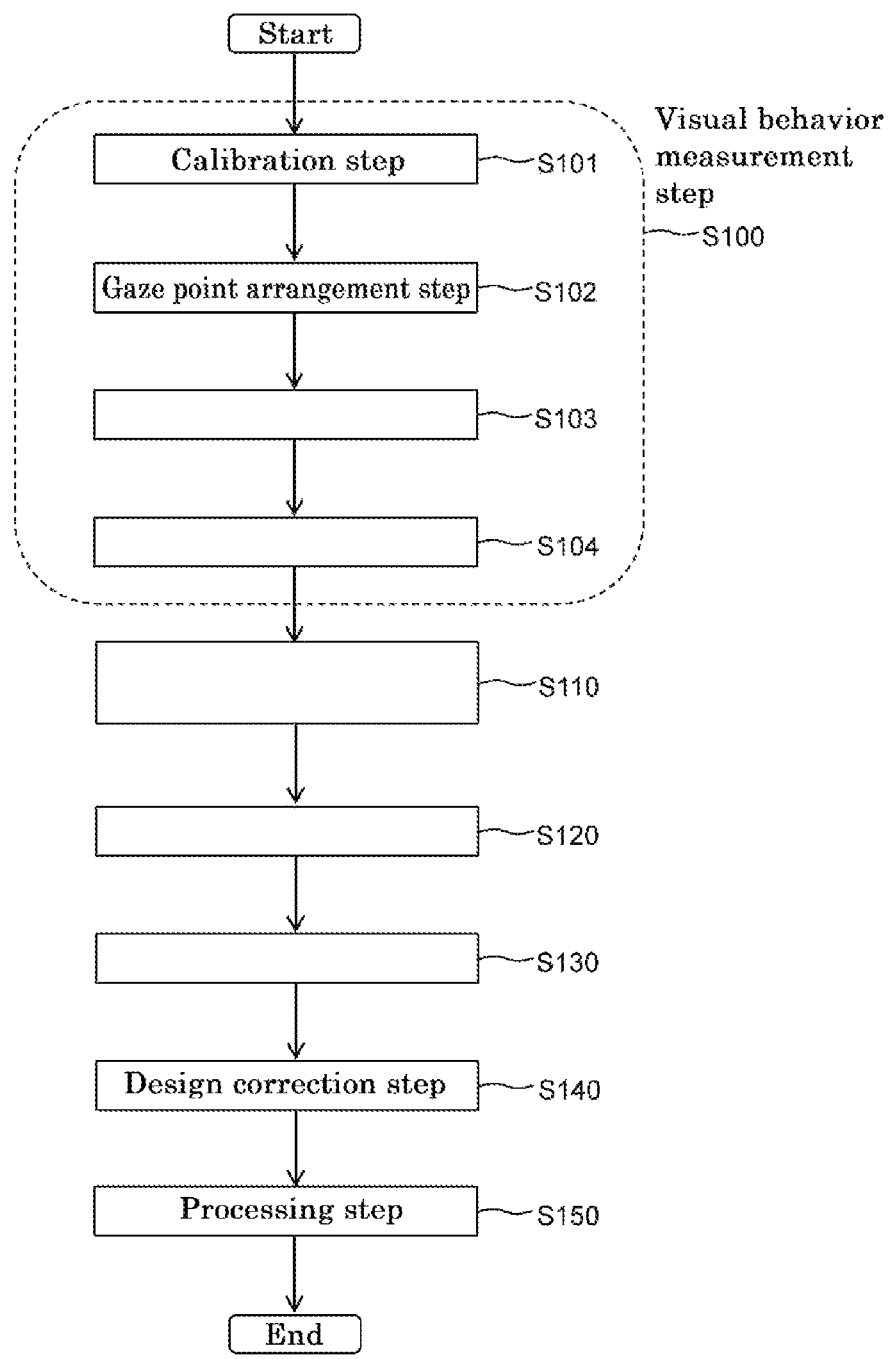
FIG. 1 is a flowchart showing an example of a method for manufacturing a progressive power lens according to a first embodiment.

FIG. 1 is a flowchart showing an example of the method for manufacturing a progressive power lens according to the present embodiment. As shown in FIG. 1, the method for manufacturing a progressive power lens according to the present embodiment includes a visual behavior measurement step S100, a line-of-sight passage position and reactive accommodation amount ascertainment step S110, a reactive accommodation amount judgement step S120, a correction method determination step S130, a design correction step S140, and a processing step S150, for example.

Visual Behavior Measurement Step S100

As shown in FIG. 1, the visual behavior measurement step S100 includes a calibration step S101, a gaze point arrangement step S102, a head rotation amount ascertainment step S103, and an eyeball rotation amount ascertainment step S104, for example.

In the visual behavior measurement step S100, visual behavior of a subject 10 who is wearing a progressive power lens is measured. In the visual behavior measurement step S100, it is preferable to measure visual behavior with respect to objects that are at different distances in the forward depth direction in a sagittal plane of the subject 10. More specifically, it is preferable to measure head rotation amounts θ and eyeball rotation amounts φ that are generated by the subject 10 in the sagittal plane of the subject 10 when gazing at objects that are at different distances in the forward depth direction.

In the present specification, rotation of an eyeball means rotation of an eyeball that occurs when a person looks up or down, such as downward rotation (infraversion) of an eyeball referred to in JIS T 7337:2020 Annex JA, for example, rather than movement (torsion) of an eyeball around a rotation axis that is a front-rear axis of the eyeball, and an angle that is generated in a vertical plane, or preferably in the midsagittal plane as a result of this movement will be referred to as an eyeball rotation amount. Also, rotation of the head means upward or downward movement of the head that occurs when a person looks up or down by bending or stretching the neck, and an angle that is generated in a vertical plane, or preferably in the midsagittal plane as a result of the upward or downward tilting of the head will be referred to as a head rotation amount.

Figure 2:
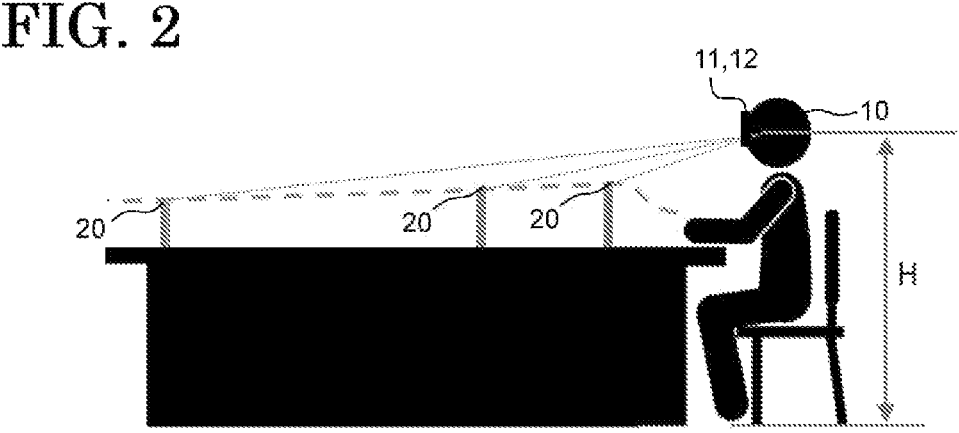
FIG. 2 is a schematic diagram showing an example of a positional relationship between a subject 10 and gaze points 20 according to the first embodiment.

FIG. 2 is a schematic diagram showing an example of a positional relationship between the subject 10 and gaze points 20. The subject 10 is wearing eyeglasses 11 that include progressive power lenses. In the present specification, the subject 10 wearing the eyeglasses 11 or the like that include progressive power lenses will also be simply referred to as the subject 10 wearing progressive power lenses, to avoid redundancy. A sensor 12 is attached to the eyeglasses 11 as a detection unit that detects a positional change of the head of the subject 10. An accelerometer can be used as the sensor 12, for example. The sensor 12 need not necessarily be attached to the eyeglasses 11, and is only required to be disposed at a position at which the sensor 12 can detect a positional change of the head of the subject 10.

In the present specification, the term "progressive power lens" refers to a lens in which the refractive power continuously changes in a part or the entirety of the single lens, and encompasses the refractive power change lens described in JIS T 7337:2020, for example. Progressive power lenses commonly encompass lenses that are called a bifocal lens, a progressive power lens for middle/near vision, a progressive additional lens, an accommodation support lens, or the like.

Calibration Step S101

In the calibration step S101, first, a height H from the floor to the eyes of the subject 10 is measured. Then, the sensor 12 is calibrated such that a posture assumed when the subject 10 horizontally looks far ahead is the reference (θ=0°) for the head rotation amount θ generated by the subject 10. As a result of this, the head rotation amount θ can be ascertained accurately in the head rotation amount ascertainment step S103, which will be described later.

In the calibration step S101, the above-described calibration is preferably performed in a state where the subject 10 is horizontally gazing at a visual target for calibration of the height H, which is set far ahead of the subject 10, for example. Also, the visual target for calibration is preferably set at a distance of 2 m or more in the forward depth direction from the subject 10 so that the subject 10 can easily maintain a horizontal line of sight. A black circle printed on a white background can be used as the visual target for calibration, for example.

Gaze Point Arrangement Step S102

In the gaze point arrangement step S102, a plurality of gaze points 20 are set at predetermined distances that differ from each other in the forward depth direction in a sagittal plane of the subject 10. In order to measure visual behavior in detail, the number of gaze points 20 is preferably at least three, and more preferably at least five. Also, the number of gaze points 20 is preferably no greater than ten so as not to increase the burden on the subject 10.

In the present specification, the term "sagittal plane" encompasses not only the midsagittal plane that equally divides the body of the subject 10 into right and left halves along the midline of the subject 10, but also all vertical planes that are parallel to the midsagittal plane and are at distances no greater than half an interpupillary distance PD of the subject 10 from the midsagittal plane, in order to take a change in the posture of the subject 10 in the left-right direction into account.

The plurality of gaze points 20 are preferably set in a real space. In this case, it is possible to measure visual behavior with respect to objects that are at different distances in the depth direction more accurately than in a case where the plurality of gaze points 20 are displayed in a display device such as a tablet to simulatively set visual targets at the different distances in the depth direction. It is preferable to use, as the gaze points 20 set in the real space, visual targets that have appropriate sizes so that the subject 10 can determine whether it is easy or hard to see the visual targets, in a short time (preferably within a few seconds), such as Landolt rings having sizes that correspond to a decimal visual acuity of 0.7 or more at distances from the subject 10 to the gaze points 20, for example. Thus, it is possible to allow the subject 10 to easily assume a posture with which the subject can see the visual targets most clearly when gazing at the gaze points 20.

When states where the subject 10 directs the line of sight to various objects in front of the subject in actual daily life are considered, it is preferable to set the plurality of gaze points 20 in a range of 0.25 m or more and 5 m or less in the forward depth direction from the subject 10 in order to reproduce visual behavior (rotation of the head and rotation of an eyeball) with respect to each object. In the case of a so-called bifocal lens, for example, it is conceivable to set at least one gaze point 20 in a range of 2 m or more and 5 m or less assuming far vision, and set at least one gaze point 20 in a range of 0.25 m or more and 0.5 m or less assuming near vision. By appropriately setting distances to the gaze points 20 according to the type of the progressive power lens worn by the subject as described above, it is possible to measure visual behavior of the subject 10 more accurately with respect to objects that are at different distances in the depth direction.

The plurality of gaze points 20 are each preferably set at a position that satisfies a relationship between an object distance and a line-of-sight direction, which is obtained based on a result of ray tracing performed for the progressive power lens worn by the subject 10. When the subject 10 gazes at each of the gaze points 20 by merely rotating eyeballs without moving the head, a position at which a refractive power D [diopter] at the position on the progressive power lens through which the line of sight passes and a distance L [m] from an eye of the subject 10 to the gaze point 20 (hereinafter also referred to as an "object distance L") satisfy a relationship of D=1/L is determined through the ray tracing, and the gaze point 20 is set at the determined position. As a result of this, the subject 10 can gaze at each of the plurality of gaze points 20 by focusing on the gaze point, irrespective of the accommodation ability of the subject 10. In the present specification, if the refractive power at the position through which the line of sight passes differs between left and right progressive power lenses, it is possible to use the refractive power of either one of the left and right progressive power lenses, or use an average value of the refractive powers.

Even if positions that satisfy the relationship of D=1/L are determined and the gaze points 20 are respectively set at the positions as described above, it is envisaged that the subject 10 will assume a posture that involves not only rotation of eyeballs but also rotation of the head when gazing at the gaze points 20. Therefore, a head rotation amount θ that is generated by the subject 10 is ascertained in the head rotation amount ascertainment step S103 described below.

Head Rotation Amount Ascertainment Step S103

In the head rotation amount ascertainment step S103, a head rotation amount θ generated by the subject 10 when gazing at each of the plurality of gaze points 20 is ascertained using the sensor 12. Specifically, a head rotation amount θ generated by the subject 10 is ascertained by letting the subject 10 gaze at the farthest gaze point 20 for 40 seconds in a natural state where both eyes are open, for example. Thereafter, the line of sight is made free for 20 seconds. The above process is performed successively to the nearest gaze point 20. The gaze points 20 need not necessarily be gazed at in the order from the farthest one to the nearest one, and may be gazed at in order from the nearest one to the farthest one.

In the head rotation amount ascertainment step S103, it is possible to use the above-described Landolt rings as the gaze points 20 and let the subject 10 discern directions in which the Landolt rings are open, in order to confirm that the subject 10 can clearly see the gaze points 20.

In the present embodiment, the plurality of gaze points 20 are set in a sagittal plane of the subject 10, and accordingly, it is preferable to consider only rotation in the up-down direction (vertical direction) for the head rotation amount $\theta$ generated by the subject 10. In this case, influence of aberration in a side portion of the progressive power lens can be eliminated, for example, and therefore, measurement of the visual behavior can be simplified. In the present specification, the head rotation amount $\theta$ is expressed using a positive value in the case of upward rotation, and is expressed using a negative value in the case of downward rotation.

In the head rotation amount ascertainment step S103, it is preferable that the subject 10 gazes at the plurality of gaze points 20 in a state of wearing a progressive power lens. Thus, it is possible to judge whether or not the visual behavior of the subject 10 is within an appropriate range with respect to variation in the additional power of the progressive power lens. Details of the judgement of the visual behavior will be described later.

Eyeball Rotation Amount Ascertainment Step S104

In the eyeball rotation amount ascertainment step S104, an eyeball rotation amount $\varphi$ that is generated by the subject 10 when gazing at each of the plurality of gaze points 20 is ascertained by determining the eyeball rotation amount $\varphi$ based on the head rotation amount $\theta$. Thus, it is possible to measure visual behavior of the subject 10 with respect to objects that are at different distances in the depth direction.

In the eyeball rotation amount ascertainment step S104, the eyeball rotation amount $\varphi$ is preferably determined based on the assumption that a line-of-sight direction (angle) when gazing at each of the plurality of gaze points 20 is realized by a sum of the head rotation amount $\theta$ and the eyeball rotation amount $\varphi$. In this case, the eyeball rotation amount $\varphi$ can be determined without using a device for measuring movement of eyeballs of the subject 10, and accordingly, the burden on the subject 10 can be reduced.

Similarly to the head rotation amount $\theta$, it is preferable to consider only rotation in the up-down direction (vertical direction) for the eyeball rotation amount $\varphi$ generated by the subject 10. In the present specification, the eyeball rotation amount $\varphi$ is expressed using a positive value in the case of upward rotation, and is expressed using a negative value in the case of downward rotation.

Through the steps described above, it is possible to measure visual behavior with respect to objects that are at different distances in the depth direction while reducing the burden on the subject 10. In order to design an eyeglass lens (in particular, a progressive power lens), it is important to measure visual behavior with respect to objects that are at different distances in the depth direction, rather than a specific viewing distance only. This is because, if the visual behavior of the subject 10 is not within an appropriate range with respect to variation in the additional power of the progressive power lens, the subject 10 has to assume an unnatural posture by excessively rotating eyeballs or excessively lowering the chin, for example, and discomfort increases. It is possible to design a progressive power lens that is appropriate for the visual behavior of the subject 10 by considering the visual behavior measured according to the present embodiment.

Line-of-Sight Passage Position and Reactive Accommodation Amount Ascertainment Step S110

In the line-of-sight passage position and reactive accommodation amount ascertainment step S110, a relationship between a line-of-sight passage position P on a surface of the progressive power lens through which a line of sight of the subject 10 passes and a reactive accommodation amount D1 that the subject 10 exhibits when the line of sight passes through the line-of-sight passage position P is determined based on the visual behavior of the subject 10 measured in the visual behavior measurement step S100.

Commonly, the accommodation ability of the subject 10 is not always fully used in each of the left and right eyes when looking at an object that is at a predetermined distance, and the accommodation ability is partially or fully exhibited depending on the conditions. In the present specification, an amount by which the accommodation ability is exhibited relative to a non-accommodation state in which the subject 10 does not exhibit the accommodation ability will be referred to as a reactive accommodation amount D1.

Figure 3:
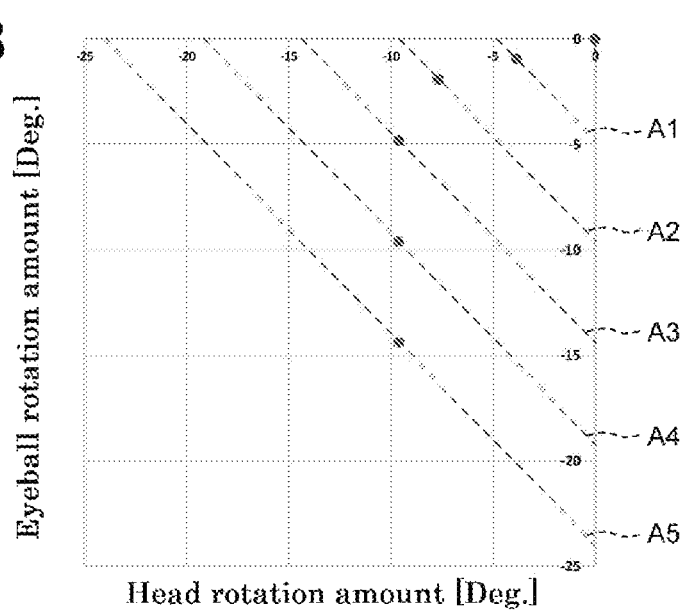
FIG. 3 is a graph showing an example of a plot of head rotation amounts θ and eyeball rotation amounts φ according to the first embodiment.

FIG. 3 is a graph showing an example of a plot of the head rotation amount $\theta$ and the eyeball rotation amount $\varphi$. In FIG. 3, the horizontal axis indicates the head rotation amount $\theta$, and the vertical axis indicates the eyeball rotation amount $\varphi$. Measurement points plotted in the graph indicate head rotation amounts $\theta$ and eyeball rotation amounts $\varphi$ ascertained for the plurality of gaze points 20, and each measurement point corresponds to a measurement result obtained for a single gaze point 20. The sum of the head rotation amount $\theta$ and the eyeball rotation amount $\varphi$ is constant on each of additional lines (A1 to A5) extending downward to the right, and the ordinate intercept of each of the additional lines (A1 to A5) indicates an eyeball rotation amount $\varphi$ of a case where the subject 10 gazes at a gaze point 20 by merely rotating eyeballs without moving the head. That is, in the case where eyeball rotation amounts $\varphi$ are determined in the eyeball rotation amount ascertainment step S104 based on the assumption that a line-of-sight direction (angle) when gazing at each of the plurality of gaze points 20 is realized by the sum of the head rotation amount $\theta$ and the eyeball rotation amount $\varphi$, measurement points are plotted on the additional lines (A1 to A5).

The line-of-sight passage position P on the surface of the progressive power lens through which a line of sight of the subject 10 passes can be uniquely identified from the eyeball rotation amount $\varphi$ of each measurement point, based on a result of ray tracing. Accordingly, the reactive accommodation amount D1 corresponding to each measurement point can be determined, because a sum (D1+D2) of the reactive accommodation amount D1 that the subject 10 exhibits when the line of sight passes through the line-of-sight passage position P and a refractive power D2 at the line-of-sight passage position P of the progressive power lens is equal to the reciprocal of the object distance L.

Reactive Accommodation Amount Judgement Step S120

In the reactive accommodation amount judgement step S120, it is judged whether or not the reactive accommodation amount D1 is within an appropriate range. More specifically, for example, it is judged whether or not at least one of a ratio (D1/Dm) and a ratio (D1/D2) is within an appropriate range, the ratio D1/Dm being a ratio of the reactive accommodation amount D1 to the maximum amplitude of accommodation Dm of the subject 10, and the ratio D1/D2 being a ratio of the reactive accommodation amount D1 to the refractive power D2 at the line-of-sight passage position P of the progressive power lens.

Figure 4:
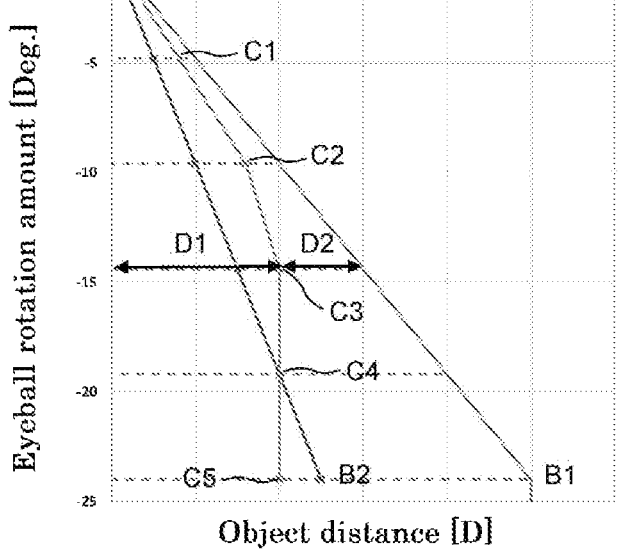
FIG. 4 is a graph showing a reactive accommodation amount D1 and a refractive power D2 at a line-of-sight passage position P of a progressive power lens according to the first embodiment.

FIG. 4 is a graph showing the reactive accommodation amount D1 and the refractive power D2 at the line-of-sight passage position P of the progressive power lens. In FIG. 4, a line B1 shows variation in the additional power along a main gaze line of the progressive power lens. The x-coordinate of each measurement point (C1 to C5) indicates the reactive accommodation amount D1 determined based on the plot shown in FIG. 3, and a difference between each measurement point (C1 to C5) and the line B1 in the horizontal axis direction indicates the refractive power D2.

In FIG. 4, a line B2 indicates that a ratio between the reactive accommodation amount D1 and the refractive power D2 is 1:1 on this line. That is, the reactive accommodation amount D1 is greater than the refractive power D2 at each measurement point on the right of the line B2, and the refractive power D2 is greater than the reactive accommodation amount D1 at each measurement point on the left of the line B2.

In the reactive accommodation amount judgement step S120, a judgement condition may be that the ratio (D1/D2) of the reactive accommodation amount D1 to the refractive power D2 at the line-of-sight passage position P of the progressive power lens is no greater than 1, for example. This is because, if the ratio (D1/D2) is greater than 1, there is a possibility that the variation in the additional power of the progressive power lens is not used effectively. In FIG. 4, three measurement points (C1 to C3) do not satisfy the judgement condition described above.

In the reactive accommodation amount judgement step S120, a judgement condition may be that the ratio (D1/Dm) of the reactive accommodation amount D1 to the maximum amplitude of accommodation Dm of the subject 10 is no greater than 0.5, for example. This is because, if the ratio (D1/Dm) is greater than 0.5, there is a possibility that a burden on the subject 10 increases. The maximum amplitude of accommodation Dm of the subject 10 can be measured using a known method.

Each judgement condition in the reactive accommodation amount judgement step S120 may be changed as necessary, or a plurality of judgement conditions may also be set.

In the reactive accommodation amount judgement step S120, it is determined that the reactive accommodation amount D1 is not within an appropriate range in a case where more than 40% (preferably more than 20%, and more preferably at least one) of the plurality of measurement points do not satisfy any of the judgement conditions, for example. That is, it is determined that the visual behavior of the subject 10 is not within an appropriate range with respect to the variation in the additional power of the progressive power lens and there is a possibility that the subject 10 cannot use the progressive power lens comfortably. In this case, a method for correcting the progressive power lens is determined in the correction method determination step S130, which will be described later, such that a larger number of measurement points satisfy the judgement conditions, for example.

Alternatively, in the reactive accommodation amount judgement step S120, it is also possible to determine that the reactive accommodation amount D1 is not within an appropriate range in a case where a measurement point largely deviates from a trend of the visual behavior of the subject 10, for example. More specifically, it is also possible to find a regression line for the plurality of measurement points shown in FIG. 4 using the least squares method, and determine that the reactive accommodation amount D1 is not within an appropriate range in a case where there is a measurement point for which an error from the regression line is greater than a predetermined value, for example. In this case, it is also possible to design the progressive power lens so as to change the additional power in a region of the progressive power lens that corresponds to the measurement point for which the error is greater than the predetermined value, for example. If the progressive power lens is designed as described above, it is expected that the subject 10 will be able to use the progressive power lens with more natural visual behavior.

In the reactive accommodation amount judgement step S120, it is determined that the reactive accommodation amount D1 is within an appropriate range in a case where 60% or more (preferably 80% or more, and more preferably 100%) of the plurality of measurement points satisfy at least one (preferably all) of the judgement conditions, for example. That is, it is determined that the visual behavior of the subject 10 is within an appropriate range with respect to the variation in the additional power of the progressive power lens and the subject 10 can use the progressive power lens comfortably.

In the present embodiment, the correction method determination step S130, the design correction step S140, and the processing step S150 may be omitted. In this case, whether or not the progressive power lens is appropriate for the visual behavior of the subject 10 can be determined through the steps described above. That is, the method for manufacturing a progressive power lens according to the present embodiment can also be performed as a method for judging a progressive power lens.

Correction Method Determination Step S130

In the correction method determination step S130, a correction method for correcting the progressive power lens is determined based on a result of judgement made in the reactive accommodation amount judgement step S120. Specifically, the correction method for correcting the progressive power lens is determined if it is determined that the reactive accommodation amount D1 is not within an appropriate range, for example.

In the correction method determination step S130, a correction amount of the additional power of the progressive power lens is determined so as to reduce the ratio (D1/Dm) of the reactive accommodation amount D1 to the maximum amplitude of accommodation Dm of the subject 10 or reduce the ratio (D1/D2) of the reactive accommodation amount D1 to the refractive power D2 at the line-of-sight passage position P of the progressive power lens, for example. More specifically, the correction amount is determined so as to increase the additional power in the vicinity of a measurement point at which the ratio (D1/Dm) is greater than 0.5 or the ratio (D1/D2) is greater than 1, for example. Alternatively, in the correction method determination step S130, it is also possible to determine a correction method that includes correction of at least one of a progressive change start point and a progressive change end point of the progressive power lens, for example.

Design Correction Step S140

In the design correction step S140, the design of the progressive power lens is corrected based on the correction method determined in the correction method determination step S130. Thus, it is possible to design a progressive power lens that is appropriate for the visual behavior of the subject 10.

In the present embodiment, the processing step S150 may be omitted. That is, the method for manufacturing a progressive power lens according to the present embodiment can also be performed as a method for designing a progressive power lens.

Processing Step S150

In the processing step S150, the progressive power lens is processed based on the design corrected in the design correction step S140. Thus, it is possible to manufacture a progressive power lens that is appropriate for the visual behavior of the subject 10.

(2) Progressive Power Lens Design System

Next, a progressive power lens design system 100 according to the present embodiment will be described.

Figure 5:
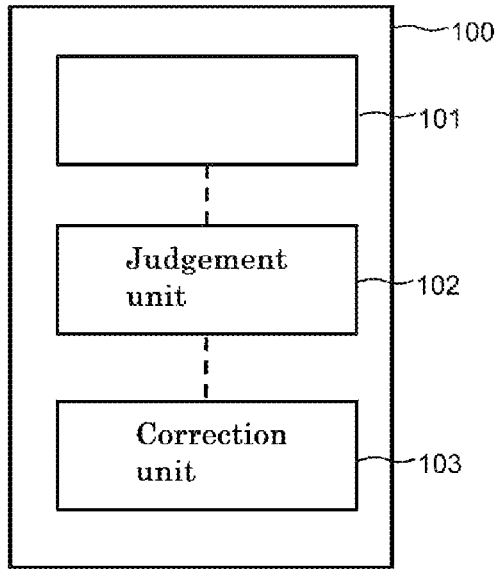
FIG. 5 is a block diagram showing a schematic configuration of a progressive power lens design system 100 according to the first embodiment.

FIG. 5 is a block diagram showing a schematic configuration of the progressive power lens design system 100 according to the present embodiment. As shown in FIG. 5, the progressive power lens design system 100 according to the present embodiment includes a line-of-sight passage position and reactive accommodation amount ascertainment unit 101, a judgement unit 102, and a correction unit 103, for example. The progressive power lens design system 100 is configured to design a progressive power lens, and is installed in a factory of an eyeglass lens manufacturer, for example.

The line-of-sight passage position and reactive accommodation amount ascertainment unit 101 is configured to ascertain a relationship between a line-of-sight passage position P on a surface of the progressive power lens through which a line of sight of the subject 10 passes and a reactive accommodation amount D1 that the subject 10 exhibits when the line of sight passes through the line-of-sight passage position P, based on visual behavior of the subject 10 wearing the progressive power lens. The visual behavior of the subject 10 is measured using the method described above regarding the visual behavior measurement step S100, for example, and is input to the line-of-sight passage position and reactive accommodation amount ascertainment unit 101 directly or via a network. A computer that executes a predetermined program as necessary can be used as the line-of-sight passage position and reactive accommodation amount ascertainment unit 101, for example.

The judgement unit 102 is configured to judge whether or not the reactive accommodation amount D1 is within an appropriate range, based on the relationship between the line-of-sight passage position P and the reactive accommodation amount D1 ascertained by the line-of-sight passage position and reactive accommodation amount ascertainment unit 101. The judgement unit 102 can use the judgement conditions described above regarding the reactive accommodation amount judgement step S120 to judge the reactive accommodation amount D1. A computer that executes a predetermined program as necessary can be used as the judgement unit 102, for example.

The correction unit 103 is configured to correct the design of the progressive power lens based on a result of judgement made by the judgement unit 102. A computer that executes a predetermined program as necessary can be used as the correction unit 103, for example.

The line-of-sight passage position and reactive accommodation amount ascertainment unit 101, the judgement unit 102, and the correction unit 103 may be connected to each other via a network, or may be provided in the same computer.

It is possible to design a progressive power lens that is appropriate for the visual behavior of the subject 10 by using the progressive power lens design system 100 configured as described above.

Second Embodiment of the Present Invention

Next, a second embodiment of the present invention will be described mainly about aspects that differ from the first embodiment. Elements that are substantially the same as those described in the first embodiment are denoted with the same reference numerals as those used in the first embodiment, and descriptions thereof are omitted.

Figure 6:
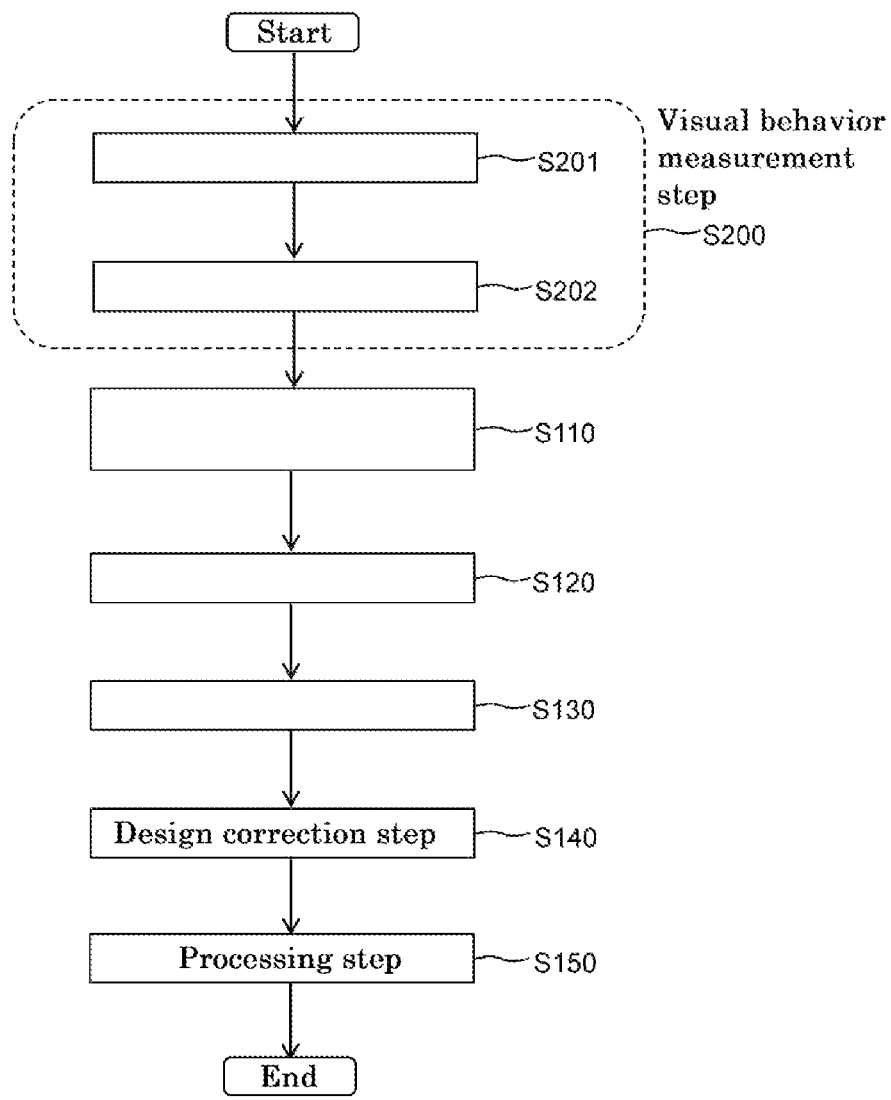
FIG. 6 is a flowchart showing an example of a method for manufacturing a progressive power lens according to a second embodiment.

FIG. 6 is a flowchart showing an example of a method for manufacturing a progressive power lens according to the present embodiment. As shown in FIG. 6, the method for manufacturing a progressive power lens according to the present embodiment differs from the first embodiment in a visual behavior measurement step S200.

Visual Behavior Measurement Step S200

As shown in FIG. 6, the visual behavior measurement step S200 includes an image capturing device arrangement step S201 and a pupil position imaging step S202, for example.

Image Capturing Device Arrangement Step S201

Figure 7:
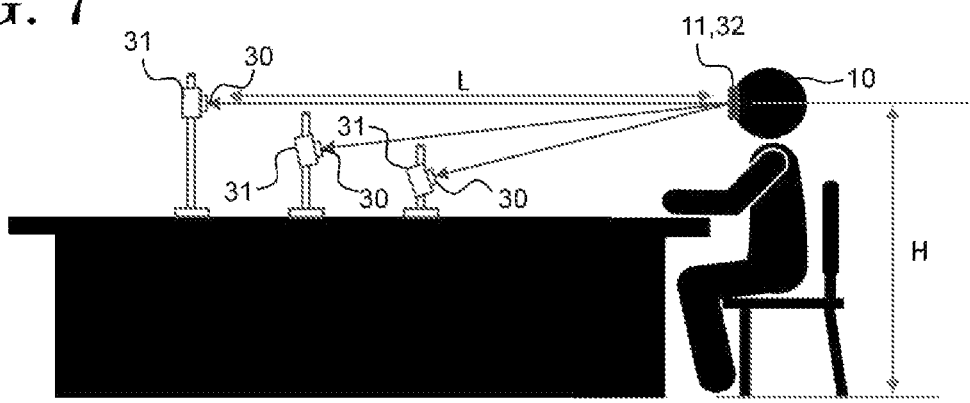
FIG. 7 is a schematic diagram showing an example of a positional relationship between a subject 10 and measurement positions 30 according to the second embodiment.

In the image capturing device arrangement step S201, an image capturing device 31 is arranged at a predetermined measurement position 30. FIG. 7 is a schematic diagram showing an example of a positional relationship between the subject 10 and measurement positions 30. Similarly to the first embodiment, the subject 10 is wearing eyeglasses 11 that include progressive power lenses. A distance meter 32 that calculates a gaze distance to an object is attached to the eyeglasses 11. A digital camera that includes a stroboscopic light emission device, an imaging element, an image memory, a computer for performing image processing, and the like can be used as the image capturing device 31, for example.

Pupil Position Imaging Step S202

In the pupil position imaging step S202, an image of the position of a pupil of the subject 10 gazing at the measurement position 30 is captured using the image capturing device 31 such that a positional relationship between the pupil and an eyeglass frame is apparent. For example, it is conceivable to mark a suitable reference point on the eyeglass frame or capture the image such that at least half of the eyeglass frame is entirely included in the range of the captured image. Also, an object distance L from an eye of the subject 10 to the measurement position 30 is calculated using the distance meter 32.

It is preferable to repeatedly perform the image capturing device arrangement step S201 and the pupil position imaging step S202 a plurality of times by changing the measurement position 30. Thus, it is possible to measure visual behavior with respect to objects that are at different distances. Also, the image capturing device 31 is preferably arranged directly opposite to the face of the subject 10 in these steps.

Line-of-Sight Passage Position and Reactive Accommodation Amount Ascertainment Step S110

A line-of-sight passage position P on a surface of the progressive power lens through which a line of sight of the subject 10 passes can be calculated from the position of the pupil of the subject 10 that is imaged in the pupil position imaging step S202. Accordingly, the reactive accommodation amount D1 can be determined similarly to the first embodiment, because a sum (D1+D2) of the reactive accommodation amount D1 that the subject 10 exhibits when the line of sight passes through the line-of-sight passage position P and a refractive power D2 at the line-of-sight passage position P of the progressive power lens is equal to the reciprocal of the object distance L.

Reactive Accommodation Amount Judgement Step S120

Figure 8:
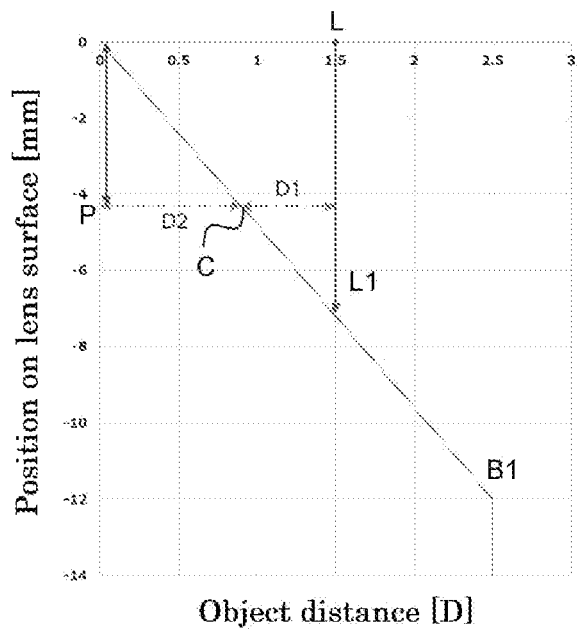
FIG. 8 is a graph showing the reactive accommodation amount D1 and the refractive power D2 at the line-of-sight passage position P of a progressive power lens according to the second embodiment.

FIG. 8 is a graph showing the reactive accommodation amount D1 and the refractive power D2 at the line-of-sight passage position P of the progressive power lens. In FIG. 8, a line B1 shows variation in the additional power along the main gaze line of the progressive power lens. The line-of-sight passage position P and the object distance L to an object seen through P corresponding to the line-of-sight passage position P can be obtained from a measurement result obtained in the line-of-sight passage position and reactive accommodation amount ascertainment step S110. A point C indicates the refractive power D2 at the line-of-sight passage position P of the progressive power lens. A difference in the horizontal axis direction between the point C and a line L1 extending vertically downward from the object distance L indicates the reactive accommodation amount D1.

By comparing the reactive accommodation amount D1 and the refractive power D2 obtained as described above, it is possible to judge whether or not the reactive accommodation amount D1 is within an appropriate range, in the present embodiment as well. The subsequent steps can be performed similarly to the first embodiment, and therefore, descriptions thereof are omitted.

As described above, it is possible to manufacture a progressive power lens that is appropriate for the visual behavior of the subject 10 in the present embodiment as well. Also, similarly to the first embodiment, it is possible to judge whether or not a progressive power lens is appropriate for the visual behavior of the subject 10. Also, it is possible to design a progressive power lens that is appropriate for the visual behavior of the subject 10.

Other Embodiments of the Present Invention

Although embodiments of the present invention have been specifically described, the present invention is not limited to the embodiments described above, and various changes can be made within a scope not departing from the gist of the present invention.

For example, in the above-described embodiments, an explanation is given for the case where the visual behavior is measured in a state where the subject 10 is wearing the progressive power lens, but the visual behavior may also be measured in a state where the subject 10 is wearing an eyeglass lens for vision correction (e.g., a fixed focal lens) other than the progressive power lens or the subject 10 is not wearing an eyeglass lens. In such a case as well, it is possible to design a progressive power lens appropriate for the visual behavior of the subject 10 similarly to the above-described embodiments by measuring the visual behavior in a state where the subject 10 is not wearing the progressive power lens (i.e., in a state where the refractive power of the eyeglass lens does not vary depending on the line-of-sight direction).

In the above-described embodiment, an explanation is given for the case where the eyeball rotation amount $\varphi$ is determined in the eyeball rotation amount ascertainment step S104 based on the assumption that a line-of-sight direction (angle) when gazing at each of the plurality of gaze points 20 is realized by the sum of the head rotation amount $\theta$ and the eyeball rotation amount $\varphi$, but it is also possible to attach a sensor 12 to the position of the hip or the neck of the subject 10 and determine the eyeball rotation amount $\varphi$ taking movement of the hip or the neck of the subject 10 into account, for example. It is possible to measure the visual behavior more accurately by using the plurality of sensors 12 to detect a change in the posture when the subject 10 gazes at the gaze points 20.

It is also possible to measure the visual behavior according to the above-described embodiments a plurality of times by letting the subject 10 wear a plurality of progressive power lenses of different designs, for example. In this case, an eyeglass lens may be designed using an average value of visual behaviors (head rotation amounts $\theta$ and eyeball rotation amounts $\varphi$) obtained through the measurement performed the plurality of times, or using the most natural visual behavior (e.g., the absolute value of the head rotation amount $\theta$ is the smallest) among visual behaviors obtained through the measurement performed the plurality of times.

In the above-described first embodiment, an explanation is given for the case where the head rotation amount $\theta$ of the subject 10 is ascertained using the sensor 12, but the detection unit for detecting a positional change of the head of the subject 10 is not limited to the sensor 12. Specifically, a head image capturing device may be disposed as the detection unit on a side of the subject 10, for example. In this case, the head rotation amount $\theta$ can be ascertained similarly to the above-described first embodiment by capturing an image of the head of the subject 10 using the head image capturing device, and analyzing the captured image in the head rotation amount ascertainment step S103. A digital camera that includes a stroboscopic light emission device, an imaging element, an image memory, a computer for performing image processing, and the like can be used as the head image capturing device, for example.

LIST OF REFERENCE NUMERALS

10 Subject
11 Eyeglasses
12 Sensor
20 Gaze point
30 Measurement position
31 Image capturing device
32 Distance meter
100 Design system
101 Line-of-sight passage position and reactive accommodation amount ascertainment unit
102 Judgement unit
103 Correction unit
S100 Visual behavior measurement step
S101 Calibration step
S102 Gaze point arrangement step
S103 Head rotation amount ascertainment step
S104 Eyeball rotation amount ascertainment step
S110 Line-of-sight passage position and reactive accommodation amount ascertainment step
S120 Reactive accommodation amount judgement step
S130 Correction method determination step
S140 Design correction step
S150 Processing step
S200 Visual behavior measurement step
S201 Image capturing device arrangement step
S202 Pupil position imaging step

What is claimed is:
1. A method for designing a progressive power lens, comprising:
a step (a) of
disposing objects at different distances in a forward depth direction from a subject wearing the progressive power lens, ascertaining a line-of-sight passage position P on a surface of the progressive power lens based on a rotation of an eyeball of the subject, and determining a reactive accommodation amount D1 that the subject exhibits when a line of sight passes through the line-of-sight passage position P, based on a refractive power D2 at the line-of-sight passage position P of the progressive power lens and the reciprocal of a distance L of an object of the objects to the subject, the sum of D1 and D2 being equal to the reciprocal of the distance L of the object to the subject;

a step (b) of judging whether or not at least one of a first ratio (D1/Dm) is greater than a first predetermined threshold and/or a second ratio (D1/D2) is greater than a second predetermined threshold, the first ratio being a ratio of the reactive accommodation amount D1 to a maximum amplitude of accommodation Dm of the subject, and the second ratio being a ratio of the reactive accommodation amount D1 to the refractive power D2 at the line-of-sight passage position P of the progressive power lens;

a step (c) of determining a correction method for correcting an additional power in a vicinity of a measurement point of the progressive power lens based on a result of judgment made in the step (b) so as to reduce the first ratio when the first ratio is greater than the first predetermined threshold and/or to reduce the second ratio when the second ratio is greater than the second predetermined threshold; and a step (d) of correcting a design of the progressive power lens based on the correction method determined in the step (c).

2. The method for designing a progressive power lens according to claim 1, wherein the visual behavior includes visual behavior with respect to objects that are at different distances in a forward depth direction in a sagittal plane of the subject.

3. The method for designing a progressive power lens according to claim 1, wherein the correction method includes correction of at least one of a progressive change start point and a progressive change end point of the progressive power lens.

4. A method for manufacturing a progressive power lens, comprising:

a step (a) of disposing objects at different distances in a forward depth direction from a subject wearing the progressive power lens, ascertaining a line-of-sight passage position P on a surface of the progressive power lens based on a rotation of an eyeball of the subject, and determining a reactive accommodation amount D1 that the subject exhibits when a line of sight passes through the line-of-sight passage position P, based on a refractive power D2 at the line-of-sight passage position P of the progressive power lens and the reciprocal of a distance L of an object of the objects to the subject, the sum of D1 and D2 being equal to the reciprocal of the distance L of the object to the subject;

a step (b) of judging whether or not at least one of a first ratio (D1/Dm) is greater than a first predetermined threshold and/or a second ratio (D1/D2) is greater than a second predetermined threshold, the first ratio being a ratio of the reactive accommodation amount D1 to a maximum amplitude of accommodation Dm of the subject, and the second ratio being a ratio of the reactive accommodation amount D1 to the refractive power D2 at the line-of-sight passage position P of the progressive power lens;

a step (c) of determining a correction method for correcting an additional power in a vicinity of a measurement point of the progressive power lens based on a result of judgment made in the step (b) so as to reduce the first ratio when the first ratio is greater than the first predetermined threshold and/or to reduce the second ratio when the second ratio is greater than the second predetermined threshold;

a step (d) of correcting a design of the progressive power lens based on the correction method determined in the step (c); and a step (e) of processing the progressive power lens based on the design corrected in the step (d).

5. A system for designing a progressive power lens, comprising:

a judgment unit configured to judge whether or not at least one of a first ratio (D1/Dm) is greater than a first predetermined threshold and/or a second ratio (D1/D2) is greater than a second predetermined threshold, the first ratio being a ratio of a reactive accommodation amount D1 to a maximum amplitude of accommodation Dm of a subject, and the second ratio being a ratio of the reactive accommodation amount D1 to a refractive power D2 at a line-of-sight passage position P of the progressive power lens, based on a relationship between the line-of-sight passage position P on a surface of the progressive power lens through which a line of sight of the subject wearing the progressive power lens passes and the reactive accommodation amount D1 that the subject exhibits when the line of sight passes through the line-of-sight passage position P, the relationship being determined based on visual behavior of the subject; and a correction unit configured to correct a design of an additional power in a vicinity of a measurement point of the progressive power lens based on a result of judgment made by the judgment unit so as to reduce the first ratio when the first ratio is greater than the first predetermined threshold and/or to reduce the second ratio when the second ratio is greater than the second predetermined threshold.

6. The method for designing a progressive power lens according to claim 1, wherein in (a), head rotation amounts θ and eyeball rotation amounts φ generated by the subject are obtained when ascertaining the line-of-sight passage position P on the surface of the progressive power lens, and the line-of-sight passage position P is identified from the eyeball rotation amount φ.

7. The method for designing a progressive power lens according to claim 1, wherein in (a), a pupil position of the subject is obtained when ascertaining the line-of-sight passage position P on the surface of the progressive power lens, and the line-of-sight passage position P is identified from the pupil position.

* * * * *